(12) United States Patent
McKay et al.

(10) Patent No.: US 7,947,053 B2
(45) Date of Patent: May 24, 2011

(54) SUTURING DEVICE AND TECHNIQUE

(76) Inventors: Raymond G. McKay, South Glastonbury, CT (US); George J. Sikora, Bridgewater, MA (US)

( * ) Notice: Subject to any disclaimer, the term of this patent is extended or adjusted under 35 U.S.C. 154(b) by 745 days.

(21) Appl. No.: 11/906,960

(22) Filed: Oct. 4, 2007

(65) Prior Publication Data

US 2008/0086152 A1    Apr. 10, 2008

Related U.S. Application Data

(60) Provisional application No. 60/850,676, filed on Oct. 10, 2006.

(51) Int. Cl.
*A61B 17/10* (2006.01)
*A61B 17/04* (2006.01)
*A61B 17/12* (2006.01)

(52) U.S. Cl. .................. 606/148; 606/139; 606/144

(58) Field of Classification Search .......... 606/139, 606/144–148
See application file for complete search history.

(56) References Cited

U.S. PATENT DOCUMENTS

| | | | |
|---|---|---|---|
| 4,662,068 A | | 5/1987 | Polonsky |
| 4,827,911 A | * | 5/1989 | Broadwin et al. ............... 601/4 |
| 5,374,278 A | | 12/1994 | Chesterfield et al. |
| 5,403,331 A | | 4/1995 | Chesterfield et al. |
| 5,417,700 A | * | 5/1995 | Egan ............................ 606/144 |
| 5,452,513 A | | 9/1995 | Zinnbauer et al. |
| 5,472,654 A | | 12/1995 | Crawford |
| 5,565,122 A | | 10/1996 | Zinnbauer et al. |
| 5,782,864 A | | 7/1998 | Lizardi |
| 5,893,880 A | * | 4/1999 | Egan et al. ..................... 606/228 |
| 6,077,277 A | * | 6/2000 | Mollenauer et al. ........... 606/144 |
| 6,217,591 B1 | * | 4/2001 | Egan et al. ..................... 606/144 |
| 6,432,115 B1 | | 8/2002 | Mollenauer et al. |
| 6,488,690 B1 | * | 12/2002 | Morris et al. .................. 606/144 |
| 6,585,750 B2 | * | 7/2003 | Bonutti et al. ................. 606/232 |
| 6,596,015 B1 | * | 7/2003 | Pitt et al. ....................... 606/232 |
| 6,866,672 B2 | | 3/2005 | Mollenauer et al. |
| 6,986,774 B2 | | 1/2006 | Middleman et al. |
| 7,094,246 B2 | * | 8/2006 | Anderson et al. ............. 606/148 |

(Continued)

OTHER PUBLICATIONS

Nho, Shane J., M.D., et al.: "*Comparison of ultrasonic suture welding and traditional knot tying in a rabbit rotator cuff repair model*", J. Shoulder Elbow Surg., vol. 15, No. 5, pp. 630-638 (Sep./Oct. 2006).

(Continued)

*Primary Examiner* — (Jackie) Tan-Uyen T Ho
*Assistant Examiner* — Dianne Dornbusch
(74) *Attorney, Agent, or Firm* — Todd E. Garabedian; Jay H. Anderson; Wiggin and Dana LLP

(57) ABSTRACT

A suturing device includes a body member having proximal and distal ends and a longitudinal axis and comprising a slide and trigger slide; a tip assembly attached to the distal end and comprising: a hollow sheath having a window at its distal end; a pushrod in the hollow sheath and in mechanical communication with the slide and moveable along the axis; and a heating element sheath containing a heating element and adjacent to the hollow sheath, the heating element in mechanical and electrical communication with the trigger slide and moveable within the heating element sheath along the axis and over the window; and circuitry in electrical communication between the trigger slide and the heating element. The trigger slide activates the circuitry to heat the heating element and moves the heating element along the axis and over the window to contact a suture and thereby create a bloom of suture material.

10 Claims, 7 Drawing Sheets

U.S. PATENT DOCUMENTS

| | | | |
|---|---|---|---|
| 2003/0114864 A1* | 6/2003 | McRury et al. ............... | 606/148 |
| 2004/0002717 A1* | 1/2004 | Warden et al. ................ | 606/138 |
| 2005/0203546 A1* | 9/2005 | Van Wyk et al. ............. | 606/138 |
| 2005/0209639 A1 | 9/2005 | Gidwani et al. | |
| 2005/0228406 A1 | 10/2005 | Bose | |
| 2006/0074438 A1 | 4/2006 | Chan | |
| 2006/0200199 A1 | 9/2006 | Bonutti et al. | |
| 2006/0271101 A1* | 11/2006 | Saadat et al. ................. | 606/205 |

OTHER PUBLICATIONS

Tadje, Jared P., et al.: *"Enhancing Knot Security by Heat Treatment of Knot Ears"*, John Wiley & Sons, Inc. (1999).

* cited by examiner

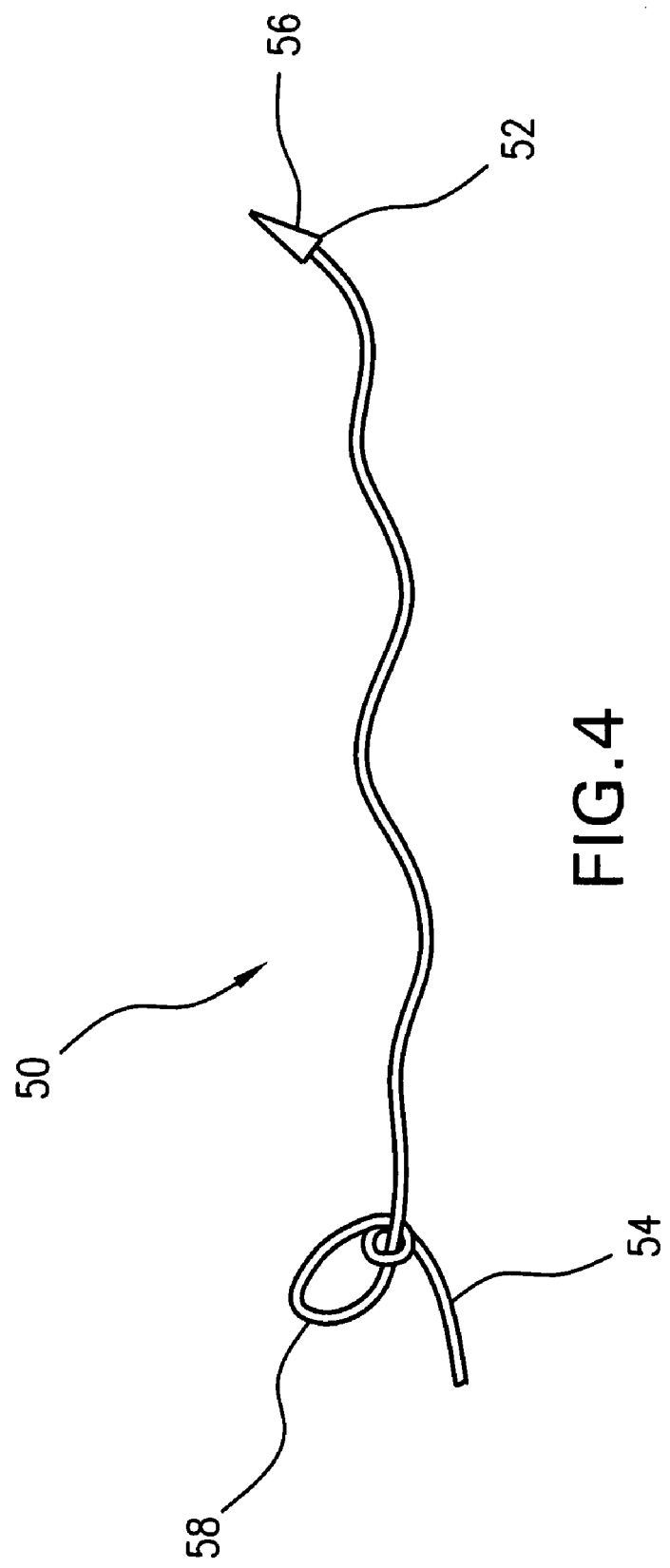

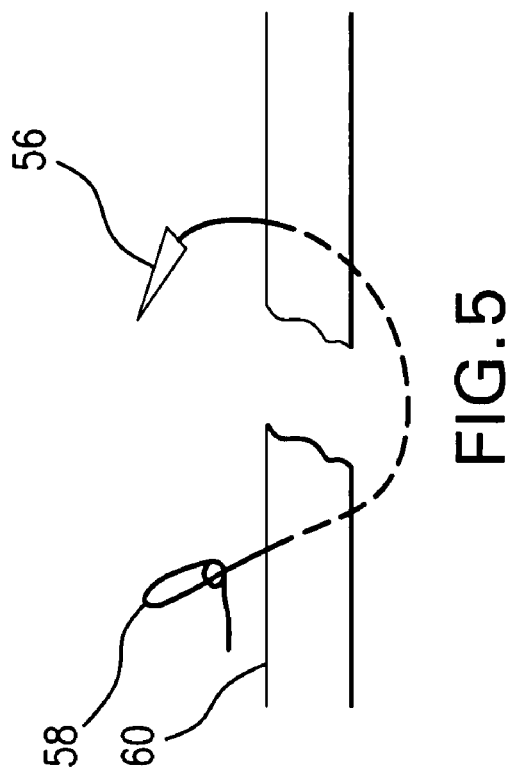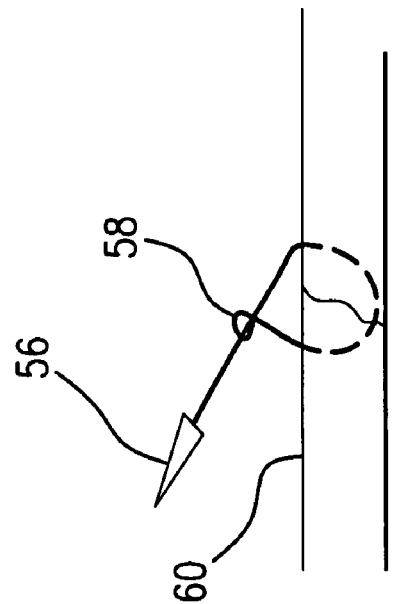

SUTURING DEVICE AND TECHNIQUE

CROSS-REFERENCE TO RELATED APPLICATIONS

This application claims the benefit of U.S. Provisional Patent Application Ser. No. 60/850,676 filed Oct. 10, 2006.

BACKGROUND OF THE INVENTION

1. Field of the Invention

The present invention is directed to a suturing device and method, and more particularly to a suturing device and method for creating a secure suture knot by blooming of the free suture end.

2. Brief Description of the Related Art

Suturing of body tissue is a time consuming and delicate task that generally requires skilled knot-tying by surgeons or physicians. Typically, during surgery it is necessary for a surgeon to suture tissue together to close an incision or wound. To secure the suture, a knot is tied. As related to medical procedures, knot tying is a complicated skill that is difficult to master, and many surgeons and physicians are not sufficiently trained to complete this task properly.

Several factors make surgical knot-tying difficult. First, a suture will frequently require multiple accumulated (e.g., three to five) knots in order to maintain the suture at a proper tightness, and the strength of the knot depends in large part on the surgeon's knot-tying technique. Second, all conventionally tied knots suffer varying degrees of knot-slippage and suture breakage which may weaken the suture construct. Moreover, since conventional knot-tying is done by hand, surgical suturing can be challenging when an incision is located nearby or in deep tissue areas of the body. Without a tightly secured suture knot, there is a greater risk of tissue dehiscense (e.g., splitting open) which can lead to bleeding, infection, and the possibility for revision surgery.

Due to the difficulty and high degree of expertise involved in knot tying, and to decrease the need for revision surgery due to suture knot failure, a wide variety of approaches have been implemented to aid surgeons and physicians in preparing secure sutures.

Examples of general approaches to preparing secure sutures include, for example, throwing multiple hitches when tying a knot; applying glue or adhesive to a knot; twisting, fusing, melting or welding together suture ends; use of clips, anchors, barbs, or other foreign body elements to secure the sutures; and the like. In addition, devices to aid in forming a secure suture are known in the art. Representative examples include U.S. Pat. Nos. 6,866,672, 6,077,277 and 6,432,115 to Mollenauer, et al., which disclose a device for welding suture segments in lieu of tying knots in sutures applied during endoscopic surgery. The disclosed devices provide for snaring loose suture ends and drawing the suture ends into a space between heating surfaces, and provide for closing the heating surfaces to weld the suture ends together.

U.S. Pat. Nos. 5,565,122 and 5,452,513 to Zinnbauer disclose a suture cutter and method of use which is adapted to clamp, sever and cauterize a thermoplastic suture. Closing of a trigger first closes a pivotal jaw against a stationary jaw to hold the suture, and then completes a circuit to sever and cauterize the suture with radiant heat.

U.S. Pat. No. 4,662,068 to Polonsky disclose a suture fusing apparatus that has a forceps type instrument with jaws including a cutting edge and a fusing surface. The jaws are heated and closed on a suture, fusing the suture material together.

U.S. Pat. No. 5,403,331 to Chesterfield, et al. discloses a surgical device for use in a ligating procedure in which a looped suture is slidably secured by a securement member such as shrinkable tubing.

U.S. Pat. No. 5,472,654 to Crawford discloses a manually operable device used to cut a synthetic material and to singe the end of the material to prevent unraveling. This is accomplished by having a crimping assembly, cutting assembly, and burning assembly for each step.

U.S. Pat. No. 6,488,690 to Morris, et al. discloses a handheld instrument that coagulates suture knots for enhanced security by applying heat to thermoplastic materials.

Although there are a number of approaches for securing sutures, ranging from tying simple knots to sophisticated techniques such as cauterizing and soldering suture ends, what is needed in the art is a device that secures a suture in place during any procedure without the necessity of cumbersome knot tying, and can be used by any surgeon without expert knot-tying skill. The present invention is believed to be an answer to that need.

SUMMARY OF THE INVENTION

In one aspect, the present invention is directed to a suturing device comprising: a body member having a proximal end, a distal end, and a longitudinal axis positioned between the proximal and distal ends, the body member comprising a slide and a trigger slide; a tip assembly attached to the distal end of the body member and comprising: a hollow sheath having a distal end and a window positioned at the distal end; a pushrod housed in the hollow sheath, the pushrod being in mechanical communication with the slide and moveable along the longitudinal axis; and a heating element sheath containing a heating element, the heating element sheath positioned adjacent to the hollow sheath, the heating element in mechanical and electrical communication with the trigger slide, the heating element moveable within the heating element sheath and along the longitudinal axis and over the window; circuitry in electrical communication between the trigger slide and the heating element, wherein the trigger slide activates the circuitry to heat the heating element and moves the movable heating element along the longitudinal axis and over the window to contact a suture and thereby create a bloom of suture material.

In another aspect, the present invention is directed to a method of securing a suture comprising the steps of: providing the suturing device described above; positioning the distal end of suturing device to contact the knot; actuating the slide to secure the knot; actuating the trigger slide to heat the heating element and sever the suture material to and form a bloom.

The details of one or more embodiments of the invention are set forth in the accompanying drawings and the description below. Other features, objects and advantages of the invention will be apparent from the description and drawings, and from the claims.

BRIEF DESCRIPTION OF THE DRAWINGS

The invention will be more fully understood from the following detailed description taken in conjunction with the accompanying drawings in which:

FIG. 4 shows an enlarged view of a suture with a pre-tied slip knot;

FIG. 5 shows a suture being inserted into flesh;

FIG. 6 shows two pieces of flesh being held together by a suture having a slip knot;

DETAILED DESCRIPTION OF THE INVENTION

The present invention is a suturing device and method that avoids cumbersome knot tying while quickly creating a secure suture. When used in conjunction with suture materials that contain pre-staged slip knots, the device and method holds a suture in place while a moveable heating element cuts and heats the suture material to create a "bloom", thereby locking the suture in place.

The suturing device and method of the invention has the advantage of creating a secured suture without the need to throw additional alternating hitches or other knots to secure the suture. This aspect is particularly advantageous because it allows the device to be used by medical personnel who do not have surgical knot-tying skills. Another advantage of the suturing device and method of the present invention is that it can be applied to a wide variety of tissues and suturing situations, including simple flesh wounds, vascular surgeries, and bone, cartilage or muscle suturing. The device and method of the present invention may also be used during minimally invasive endoscopic or arthroscopic procedures when secure sutures need to be placed inside the body through small incisions. The suturing device and method of the present invention circumvents the use of foreign body anchors or barbs which are commonly used in non-tying suturing techniques, and which can become infected or dislodged. The suturing device of the present invention may be used with a variety of selected suture materials, including those that contain pre-tied slip knots, or those that do not contain pre-tied slip knots. In the latter case, the surgeon may choose to make their own slip knots, or may use the device and method to secure conventionally tied knots.

Figure 1:
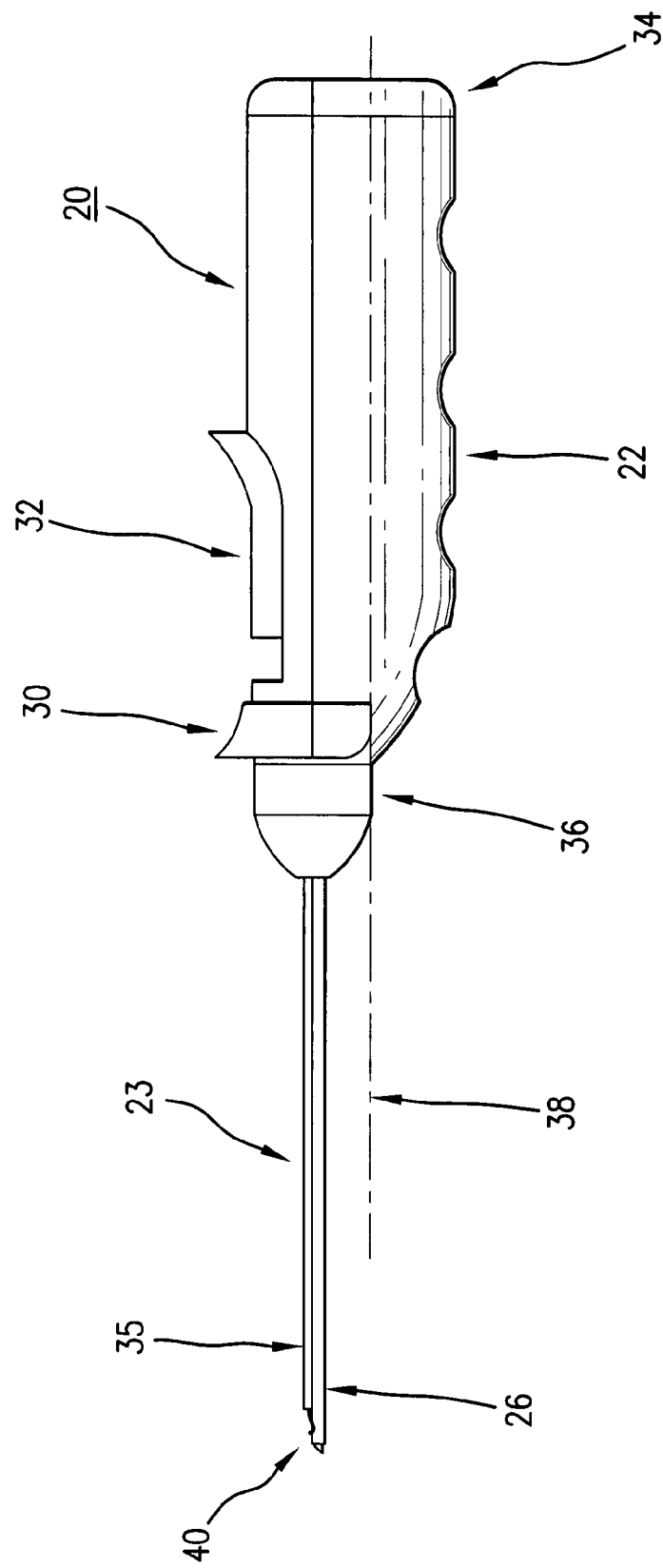
FIG. 1 shows a side view of a suturing device of the invention.

Referring to FIG. 1, the suturing device of the invention 20 in accordance with the invention is shown. In general, the device 20 includes a body member 22 that is held in the user's hand and which contains electrical and device actuation elements, and a tip assembly 23 that includes elements relating to securing the suture. These elements are discussed in greater detail below.

Body member 22 includes a proximal end 34, a distal end 36 and a longitudinal axis 38 positioned between the proximal end and the distal end and extending away from the distal end 36. As shown in FIG. 1, body member 22 is substantially cylindrical in shape, but it will be understood that other configurations may be used consistent with the practice of the invention. Body member 22 can be made of any suitable material such as plastic, nylon, metal, and the like. Body member 22 has a length in the range of about 2 inches to about 8 inches and is preferably contoured to fit into the left or right hand of the user. Trigger slide 30 and slide 32 are also positioned on body member 22 such that they can be actuated by the user's fingers when the device is in use. Body member 22 typically has a diameter sufficient to accommodate the internal electrical and mechanical components of the device (discussed in more detail below). In one embodiment, the diameter of body member 22 is in the range of between about 0.5 inch to about 2 inches, although it is to be understood that any set of dimensions may be implemented.

As shown in FIG. 1, tip assembly 23 is attached to distal end 36 of the body member 22 and extends parallel to the longitudinal axis 38. As will be appreciated by those skilled in the art, the length of tip assembly 23 may be configured to comply with a particular surgery or location of a surgical procedure. For example, a shorter tip assembly 23 is preferable when sealing a wound on the surface of the skin because a shorter device is generally easier to manipulate. On the other hand, a longer tip assembly 23 is preferable when performing surgeries deep within body tissue, or during arthroscopic and/or endoscopic procedures through small incisions.

Figure 2:
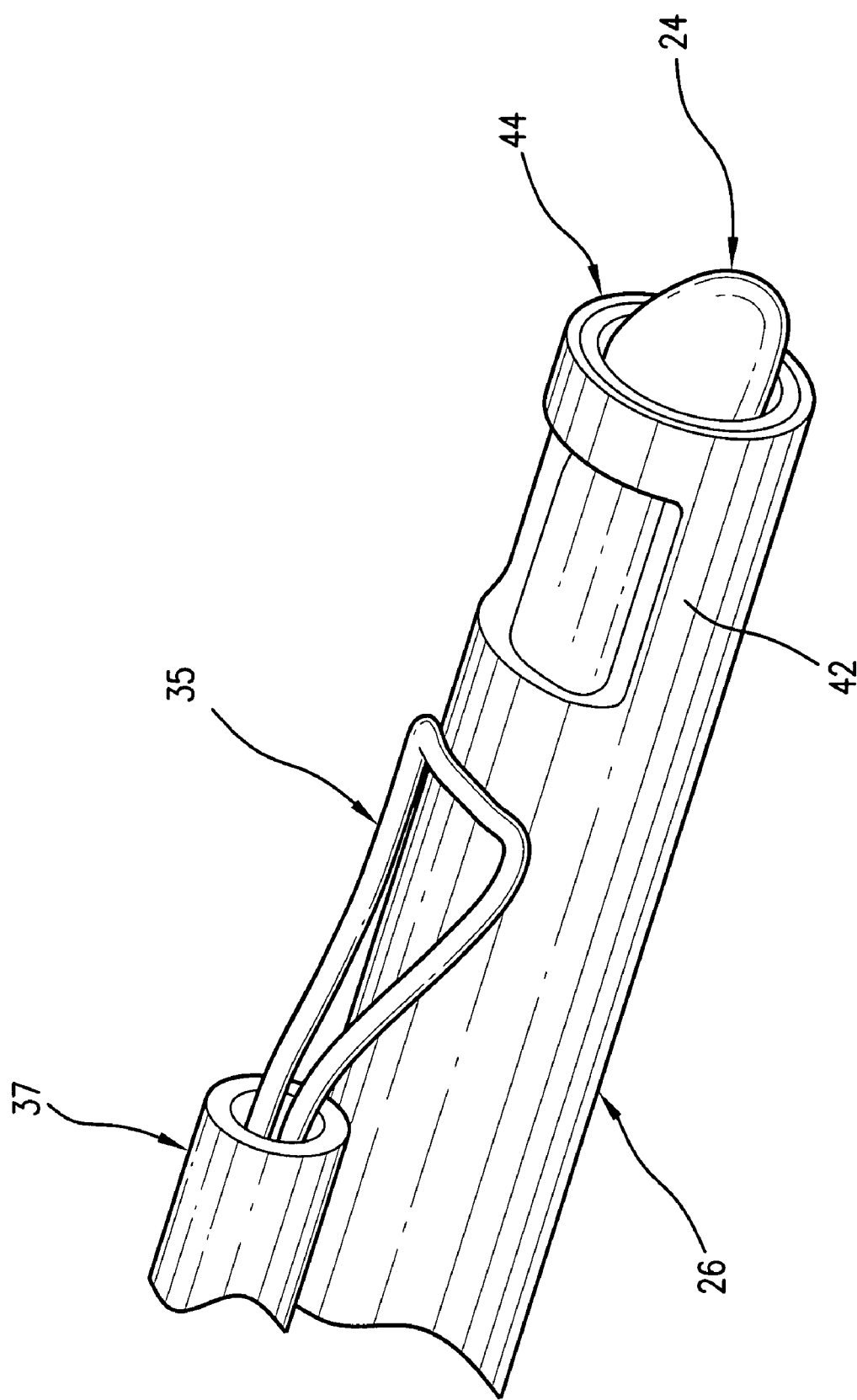
FIG. 2 shows an enlarged view of one end of the tip assembly of the device of the invention.

As shown in FIGS. 1 and 2, tip assembly 23 includes a longitudinal hollow sheath 26 which houses a moveable pushrod 24. Moveable pushrod 24 is mechanically connected to slide 32 and is advanced parallel to the longitudinal axis 38 by actuating slide 32. Tip assembly 23 also includes a moveable heating element 35 contained within a heating element sheath 37 and attached to the outer surface of sheath 26. Moveable heating element 35 is in electrical communication with the circuitry contained in body member 22, and may be activated by actuation of trigger slide 30. Additionally, moveable heating element 35 is in mechanical communication with trigger slide 30 and may be advanced parallel to the longitudinal axis 38 and through heating element sheath 37 by actuation of trigger slide 30. The distal end 40 of tip assembly 23 is the location where the suture is secured, and is shown in more detail in FIG. 2. As will be appreciated by one of skill in the art, the specific location of the pushrod and heating element may vary, for example, either may be located inside or outside hollow sheath 26.

Figure 3:
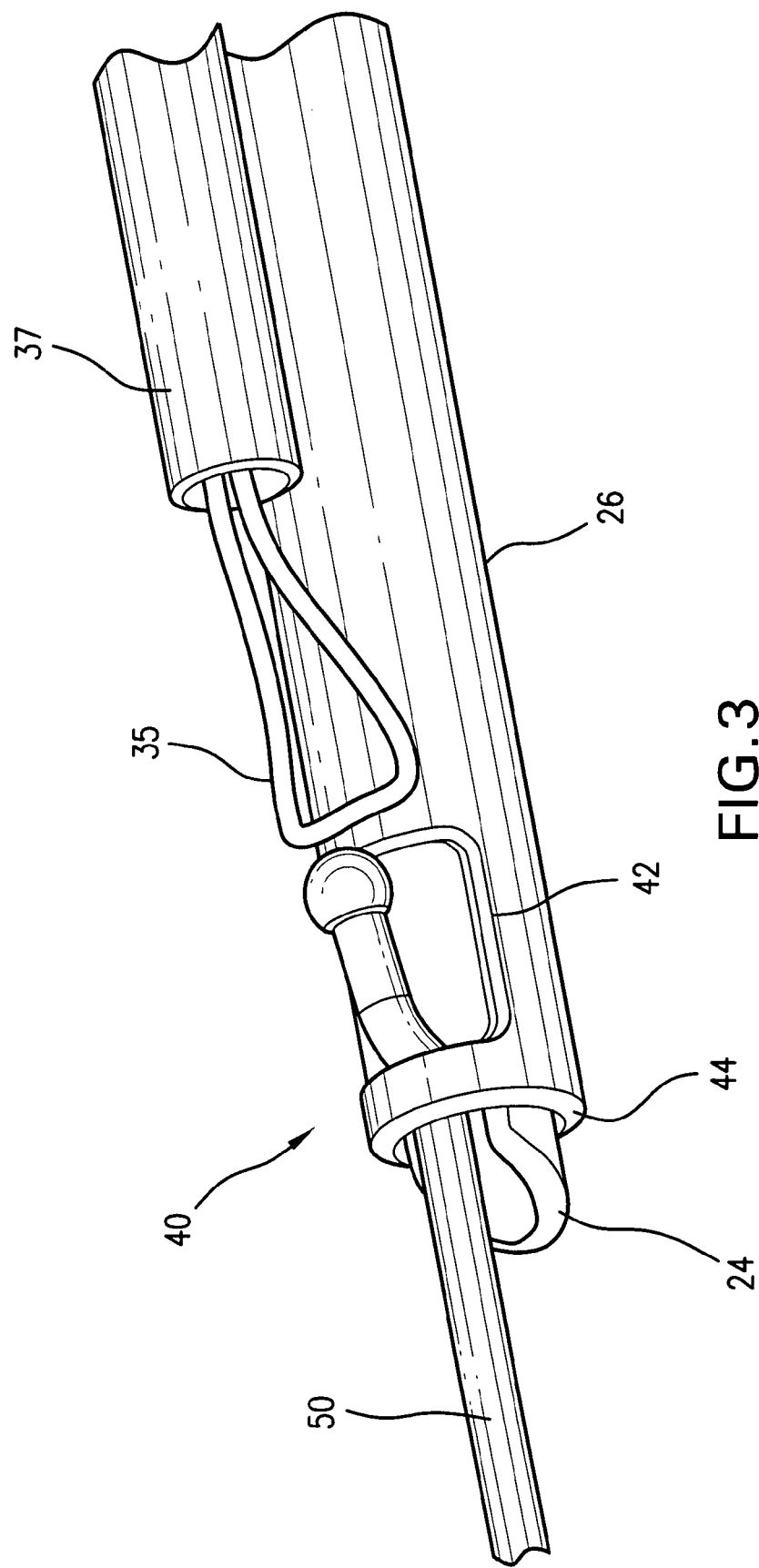
FIG. 3 shows another enlarged view of one end of the tip assembly of the device of the invention.

As shown in FIGS. 2 and 3, where like reference numerals refer to like elements, the distal end 40 of tip assembly 23 includes a window 42 where suture material 50 is passed. Sheath 26 is preferably sized to accommodate moveable pushrod 24. In one embodiment, the diameter of sheath 26 ranges from about 1 mm to about 10 mm in diameter. In addition, window 42 may be any size that can accommodate the selected suture material, for example 1-5 mm in width. Typically, sheath 26 is made from metal, and preferably metals appropriate for surgical devices such as stainless steel.

Pushrod 24 is designed to hold a slip knot suture in place during a suturing procedure. Pushrod 24 operates in any way that, when advanced by slide 32, it places pressure on the suture construct to keep it in place and stabilize the free end of the suture for blooming. The distal end of pushrod 24 has a beveled, relief angled, or grooved surface that will facilitate positioning of the free suture end through the distal opening 44 of sheath 26, thereby causing the suture to exit from the window 42 of sheath 26. Typically, pushrod 24 is made from metal, and preferably metals appropriate for surgical devices such as stainless steel. Alternative materials such as plastic, ceramic or other atraumatic, non-abrasive, and non-conductive materials known in the surgical arts may also be used.

Pushrod 24 is in mechanical connection with slide 32. Slide 32 is a switch that actuates pushrod 24, and will be appreciated in the art to encompass other switches designed to achieve the same purpose, such as a finger trigger, a button, switch, or any other mechanism that is mechanically connected to the pushrod 24. Moving slide 32 towards distal end 36 of body member 22 causes advancement of pushrod 24 along longitudinal axis 38 and against a suture material, preventing retrograde slippage of the suture and locking it into place. As will be appreciated by one of skill in the art, and in alternative embodiments, the mechanism that locks the suture in place may include any suitable grasping mechanism known in the art, such as a collet, notch, claw, jaws, fingers, forceps, and the like. Such grasping mechanisms are advantageous in the device and method of the present invention because they grasp the suture material firmly and lock the suture in place, subsequently allowing for suture cutting and blooming.

As indicated above, tip assembly 23 also includes a moveable heating element 35 contained within heating element sheath 37. Heating element sheath 37 is generally stationary and is attached to the outer surface of sheath 26. Moveable heating element 35 is preferably wire made of nickel chromium alloy and may be of any diameter sufficient to sever a thermoplastic suture material. Moveable heating element 35 is in electrical communication with the circuitry contained in body member 22, and may be activated by actuation of trigger slide 30. Moveable heating element 35 is also in mechanical communication with trigger slide 30 and may be advanced parallel to the longitudinal axis 38 and through heating element sheath 37 by actuation of trigger slide 30. As will be appreciated, trigger slide 30 may alternatively be other switches designed to achieve the same purpose, such as a finger trigger, a button, switch, or any other mechanism. In an alternative embodiment, heating element 35 may also include an optional external shield to protect tissue adjacent to the suturing site from thermal damage. Such external shield may be made of plastic, ceramic, or other atraumatic, non-abrasive, or non-conductive materials known in the art and would be positioned at least adjacent to heating element 35 to protect surrounding tissue.

As shown in FIG. 4, a typical suture 50 to be used with suturing device 20 has a distal end 52 and a proximal end 54. Associated with distal end 52 is a swaged needle 56 and associated with proximal end 54 is a pre-tied slip knot 58. As shown in FIGS. 5 and 6, in one embodiment, swaged needle 56 is placed through tissue 60 to be sutured and is then passed through pre-tied slip knot 58. Preformed slip knots can be purchased from commercially-available sources (e.g. Pare Surgical, Inc., Englewood, Colo.). As shown in FIG. 6, slip knot 58 is reduced to the surface of tissue 60 making a tight closure.

To use the device, the following general procedure is followed. After a pre-tied slip know is placed on the patient, the free end of the suture is positioned through the distal opening 44 of hollow sheath 26 and exits through window 42. In operation, advancement of moveable pushrod 24 with slide 32 locks the slip knot into place. Activation and advancement of trigger slide 30 heats and advances moveable heating element 35 such that heating element 35 moves over window 42. This movement by heating element 35 over window 42 severs the free suture exiting from window 42 and "blooms" the remaining suture material immediately adjacent to the slip knot.

Figure 7:
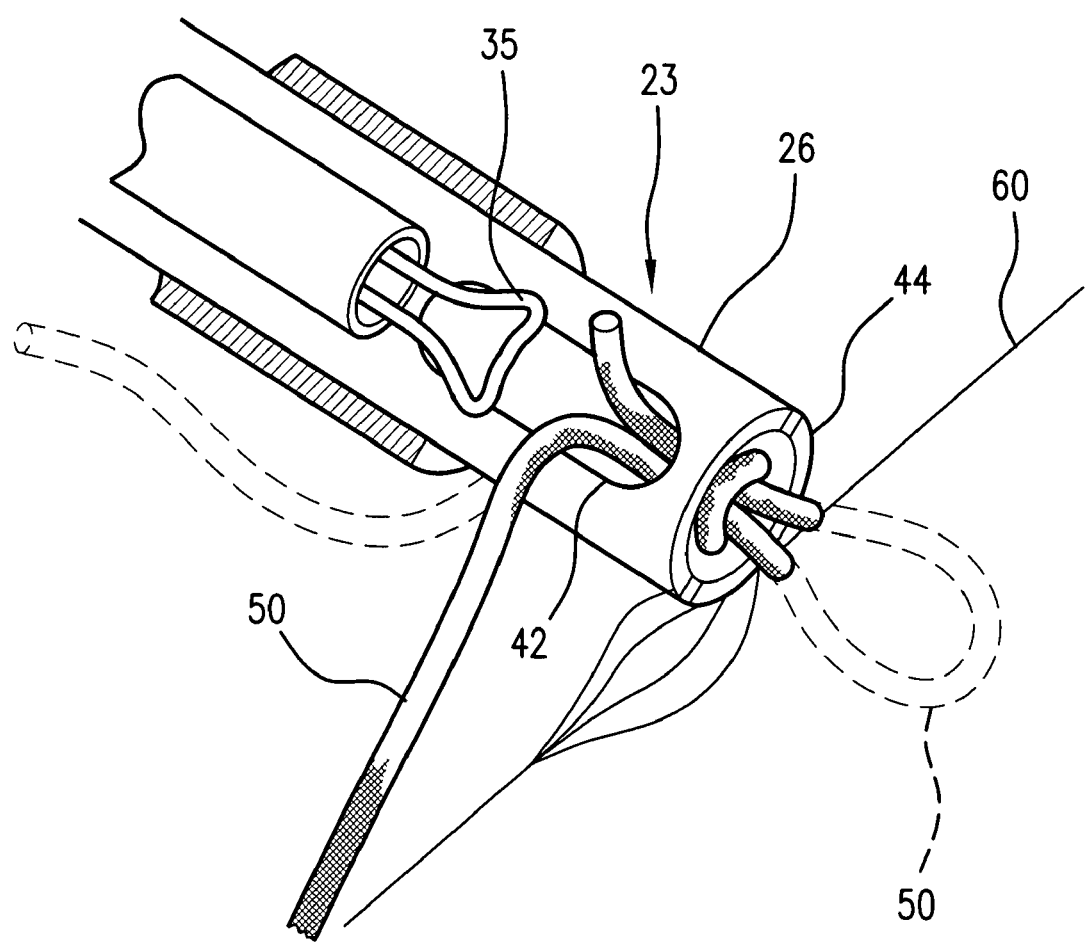
FIG. 7 shows a free end of a slip knot positioned through the end of the sheath and exiting from the window.
Figure 8:
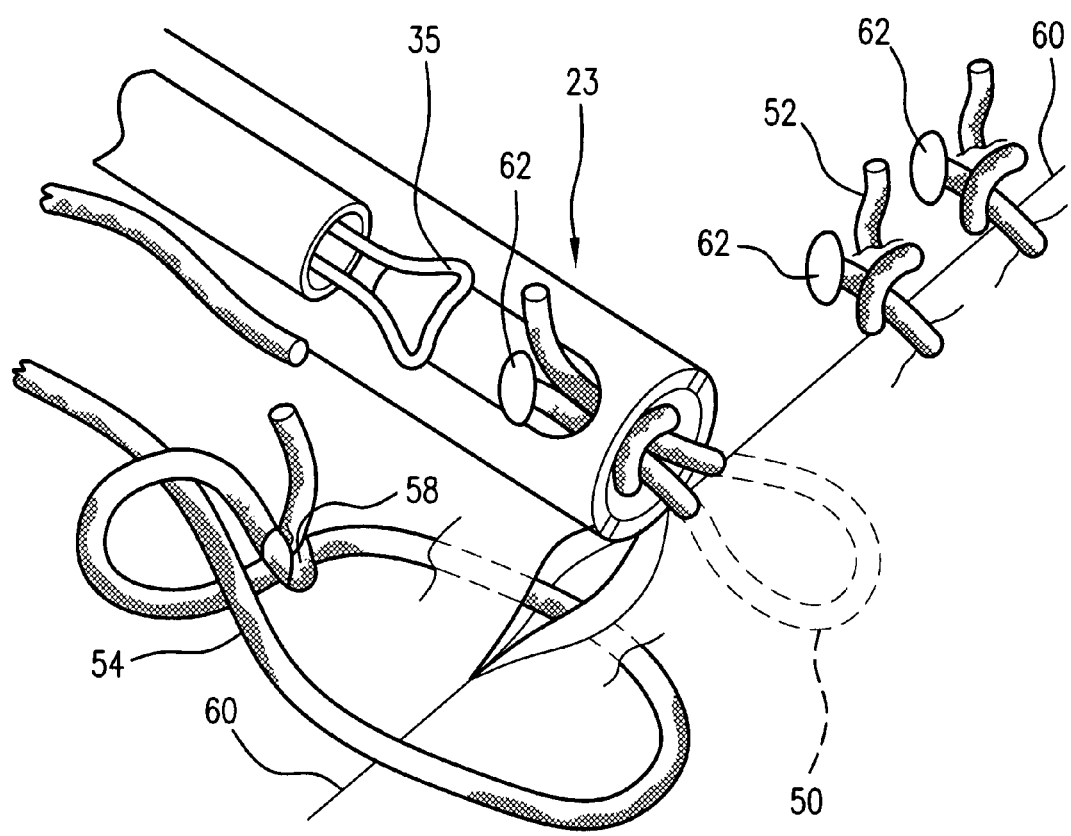
FIG. 8 shows advancement of the heating element to cut and bloom the suture material.

Suturing device 20 is shown in operation in more detail in FIGS. 7-8. FIG. 7 shows a slip knot locked in place with pushrod 24 before heat is applied to the suture. The free end of the slip knot exists from window 42. Preferably, suture 50 is held by pushrod 24 as close to the slip knot as possible, by advancement of pushrod 24 via slide 32. The beveled end of pushrod 24 facilitates passage of the free end of the suture through the distal opening 44, and subsequently exiting through window 42. The beveled surface also provides a barrier to prevent the slip knot from unraveling, thus locking it into place. The portion of suture 50 that was threaded through window 42 can be held at any angle with respect to longitudinal axis 38. In a preferred embodiment, the tip assembly 23 of the device is held in close proximity with the surface of the wound to be treated thus ensuring tight closure of the wound.

Moveable heating element 35, positioned in close proximity to window 42, is in mechanical and electrical communication with power sources and trigger slide 30 located on body 22. Heating element 35 and its electrical circuitry are contained in heating element sheath 37 attached to hollow sheath 26. Heating element 35 is activated by trigger slide 30, which causes the heating element to heat by activation of electrical circuitry and forward movement over window 42.

Suture 50 may be at any angle when the device is in operation and pushrod 24 has been advanced to lock the suture in place, depending largely on the accessibility of the knot during the suturing process. During operation, trigger slide 30 is pressed to activate moveable heating element 35, and once activated, moveable heating element 35 is heated and travels along the longitudinal axis 38 until it comes into contact with suture 50. When contact is made between moveable heating element 35 and suture 50, the heat from the moveable heating element causes the suture to sever on contact. Simultaneously, as suture 50 is severed, a "bloom" is formed on the free end by the melted suture material. The bloom functions to lock the suture in place and prevents the suture construct from slipping, failing, or unraveling.

The term "bloom" is defined herein to mean thermal deformation of the suture material to create a dimensional mechanical interference whereby the "bloom" end is enlarged and cannot pass through the small space where the knot is tied. This interference results in a secure suture construct that cannot slip or fail. Generally all absorbable and non-absorbable thermoplastic sutures will melt at sufficiently high enough temperatures to cause a bloom to form. An intrinsic part of the blooming process is that melted polymer will form a liquid ball on the unheated part of adjacent solidified suture to minimize surface tension. Movement of the heating element along the unheated suture will cause the liquid ball to grow larger as more liquid polymer accumulates. As the polymer cools, the molten bloom solidifies and forms a mechanical barrier that prevents the suture construct from failing. Melting temperatures vary depending on the type of suture material, but generally range from about 170° C. to about 700° C., and the temperature may be controlled by the addition of an internal or external rheostat or similar power modulating device. The power source for the moveable heating element 35 can be any electrical power source such as internally located batteries, AC power, or the like. In other embodiments, alternative energy sources may also be used to sever the suture material, including radiofrequency (RF) or laser sources. In addition, the hollow nature of sheath 26 provides an evacuation route for any gaseous material that is generated by the heating/blooming process. Additional channels or orifices located within sheath 26 and adjacent to pushrod 24 may be included for additional gas evacuation.

Suture 50 used in conjunction with the device of the present invention may be any absorbable or non-absorbable thermoplastic suture material as long as it is deformable by application of heat. Examples of suitable suture materials include suture materials made from polyamide (nylon), polyester (Dacron), polypropylene (Prolene), polyethylene, ultra high molecular weight polyethylene, polybutylester, polyglycolic acid, polyglactin, polydioxane, polytrimethylene carbonate, polyglecaprone, or any other polymer-based suture. Choice of size and application of any particular suture material vary but are within the skill of the ordinary practitioner. In addition, as indicated above, the device of the present invention may be used with suture material that does or does not contain pre-staged slips for forming slip knots. FIG. 4 shows one preferred embodiment of the suture material used in conjunction with the device of the present invention which contains a pre-staged slip for forming a slip knot. However, as will be appreciated by those of skill in the art, pre-staged slip knots are not required for the suture material used with the device of the present invention. In alternative embodiments, the user may tie their own slip knots or may use the device to secure conventionally tied knots by thermally blooming free suture ends.

Referring now to FIG. 8, suturing device 20 is shown during, and after the suturing procedure. Suture 54 includes slip knot 58 and are shown before they are exposed to the suturing device 20. Suture 50 is shown positioned proximal to surface 60 close to the pre-tied slip knot 58 and in the process of being secured with suturing device 20. The free end of the suture is positioned through distal opening 44 and exits through window 42. As described in detail above, moving slide 32 causes pushrod 24 to move within sheath 26, locking suture 50 in place on surface 60. Once suture 50 is held in place by pushrod 24, the user presses trigger slide 30 (see FIG. 1) and activates moveable heating element 35 which moves towards suture 50 along longitudinal axis 38. The user continues to press trigger slide 30 until it contacts suture 50. As moveable heating element 35 comes into contact with suture 50, the heat cuts the suture material and causes it to deform and create a bloom 62 of material. Once the exposed suture is bloomed, trigger slide 30 is released, and moveable heating element 35 cools and retracts. Coincidentally, release of slide 30 allows retraction of pushrod 24 allowing for removal of suturing device 20 away from surface 60. As suture 50 cools, the material hardens leaving a bloom of suture material on surface 60, thereby locking the suture in place without tying a knot. Finally, sutures 52 are shown after suturing device 20 has been applied. Sutures 52 are secured by a bloom of suture material created by suturing device 20.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. A suturing device comprising:
a body member having a proximal end, a distal end, and a longitudinal axis positioned between said proximal and distal ends, said body member comprising a slide and a trigger slide;
a tip assembly attached to said distal end of said body member and comprising:
a hollow sheath having an outer wall and a distal end, and a window in the outer wall proximate to said distal end;
a pushrod housed in said hollow sheath, said pushrod being in mechanical communication with said slide and moveable along said longitudinal axis; and
a heating element sheath containing a heating element, said heating element sheath positioned exterior to said hollow sheath and adjacent to the outer wall of said hollow sheath, said heating element in mechanical and electrical communication with said trigger slide, said heating element moveable within said heating element sheath and along said longitudinal axis and exterior to said hollow sheath over said window;
circuitry in electrical communication between said trigger slide and said heating element, wherein said trigger slide activates said circuitry to heat said heating element and moves said movable heating element along said longitudinal axis and over said window to contact a portion of a suture exiting said window and thereby create a bloom of suture material.

2. The suturing device of claim 1, wherein said pushrod comprises an end that is beveled, relief angled, or grooved.

3. The suturing device of claim 1, wherein said pushrod further comprises a grasping mechanism selected from the group consisting of collet, notch, claw, jaws, fingers, and forceps.

4. The suturing device of claim 1, further comprising a power source housed in said body member.

5. The suturing device of claim 1, further comprising a power modulating device.

6. The suturing device of claim 5, wherein said power modulating device is a rheostat.

7. The suturing device of claim 1, wherein said heating element comprises a radiofrequency or laser source.

8. The suturing device of claim 1, wherein said hollow sheath and said pushrod are individually constructed of stainless steel.

9. The suturing device of claim 1, wherein said suture comprises a material selected from the group consisting of polyamide, polyester, polypropylene, polyethylene, ultra high molecular weight polyethylene, polybutylester, polyglycolic acid, polyglactin, polydioxane, polytrimethylene carbonate, polyglecaprone, and combinations thereof.

10. The suturing device of claim 1, further comprising an external shield positioned adjacent to said heating element.

* * * * *